United States Patent
Sagehashi et al.

(10) Patent No.: US 6,869,428 B2
(45) Date of Patent: Mar. 22, 2005

(54) OPHTHALMOLOGIC PHOTOCOAGULATOR AND PHOTOCOAGULATION METHOD THEREOF

(75) Inventors: Hideo Sagehashi, Tokyo (JP); Wataru Ooyagi, Tokyo (JP); Masayuki Momiuchi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 10/664,909

(22) Filed: Sep. 22, 2003

(65) Prior Publication Data

US 2004/0057119 A1 Mar. 25, 2004

(30) Foreign Application Priority Data

Sep. 20, 2002 (JP) ....................................... 2002-274270

(51) Int. Cl.⁷ .................................................. A61F 9/08
(52) U.S. Cl. ................................. 606/4; 128/898; 606/6
(58) Field of Search ........................... 128/898; 606/4–6

(56) References Cited

U.S. PATENT DOCUMENTS

| | | | | | |
|---|---|---|---|---|---|
| 5,098,426 | A | * | 3/1992 | Sklar et al. ..................... | 606/5 |
| 5,147,349 | A | * | 9/1992 | Johnson et al. ................. | 606/4 |
| 6,312,423 | B1 | * | 11/2001 | Ota et al. ....................... | 606/4 |
| 6,530,918 | B1 | * | 3/2003 | Ueno et al. ..................... | 606/10 |
| 6,540,391 | B2 | * | 4/2003 | Lanzetta et al. ............. | 362/553 |
| 6,567,597 | B2 | * | 5/2003 | Sasaoka et al. ............. | 385/123 |
| 6,711,185 | B2 | * | 3/2004 | Steffens ....................... | 372/27 |
| 2003/0149425 | A1 | * | 8/2003 | Takada et al. ................. | 606/4 |

FOREIGN PATENT DOCUMENTS

JP 7-163613 6/1995

* cited by examiner

Primary Examiner—Roy D Gibson
Assistant Examiner—Henry M Johnson, III
(74) Attorney, Agent, or Firm—Armstrong, Kratz, Quintos, Hanson & Brooks, LLP

(57) ABSTRACT

An ophthalmologic photocoagulator and photoagulation method thereof in which visibility of sighting laser beam which is projected onto the eye fundus of an eye to be examined is improved and a loss in the amount of treatment laser beam can be reduced. The ophthalmologic photocoagulator includes: a treatment laser oscillator that oscillates a treatment laser beam for conducting treatment on a diseased part of the eye to be examined by photocoagulation; a sighting laser oscillator that oscillates a sighting laser beam for conducting sighting on the diseased part of the eye to be examined which is to be irradiated with the treatment laser beam; and a polarization beam splitter for combining an optical path of the treatment laser beam with an optical path of the sighting laser beam by polarization coupling. The treatment laser beam oscillating from the treatment laser oscillator and the sighting laser beam oscillating from the sighting laser oscillator have similar colors.

3 Claims, 1 Drawing Sheet

OPHTHALMOLOGIC PHOTOCOAGULATOR AND PHOTOCOAGULATION METHOD THEREOF

BACKGROUND OF THE INVENTION

1. Field of the Invention

The present invention relates to an ophthalmologic photocoagulator that conducts treatment on a diseased part of an eye to be examined by photocoagulation.

2. Description of the Related Art

Up to now, an ophthalmologic photocoagulator of a water cooling type, which is capable of continuously oscillating laser beam, has been a mainstream of the conventional ophthalmologic photocoagulator. Such an ophthalmologic photocoagulator is provided with a single laser oscillator, and uses treatment laser beam and sighting laser beam separately by inserting and removing a dense filter into and from an optical path of the laser beam. However, increase in the size of the conventional ophthalmologic photocoagulator is inevitable, causing a problem in view of spaces of a treatment room and an operating room. Note that the treatment laser beam means laser beam applied for conducting treatment on a diseased part of an eye to be examined by photocoagulation. In addition, the sighting laser beam means laser beam applied upon sighting for appropriately irradiating the diseased part with the treatment laser beam.

In view of the above-mentioned problem, a small-size ophthalmologic photocoagulators of an air cooling type that operates by power supplied through a general receptacle has been developed. Now, this type is the mainstream of ophthalmologic photocoagulators. In such an ophthalmologic photocoagulator, because laser continuous oscillation can not be made, a treatment laser oscillator that oscillates the treatment laser beam and a sighting laser oscillator that oscillates the sighting laser beam are separately provided. Here, in general, green laser beam having high energy is used as the treatment laser beam and red laser beam having low energy is used as the sighting laser beam. FIG. 3 is a schematic view showing a feature part of such an ophthalmologic photocoagulator 50.

The ophthalmologic photocoagulator 50 includes a treatment laser oscillator 51 that oscillates the green laser beam as the treatment laser beam, a sighting laser oscillator 52 that oscillates the red laser beam as the sighting laser beam, a dichroic mirror 53 for combining the optical path of the treatment laser beam with the optical path of the sighting laser beam, an optical fiber 54 composing a part of an optical system that guides laser beam to an eye to be examined, a condenser lens 55 that condenses laser beam to an incident end 54a of the optical fiber 54, and a photo diode 56 that receives a part of the treatment laser beam to monitor an output state of the treatment laser beam.

In the ophthalmologic photocoagulator 50, after sighting is focused on a diseased part on the eye fundus of the eye to be examined using the red sighting laser beam, photocoagulation on the diseased part can be conducted using the green treatment laser beam which is imaged onto the eye fundus through the same optical path as the sighting laser beam, without the treatment laser beam being deviated from the sighted portion. Accordingly, even in the small-size ophthalmologic photocoagulator in which the laser beam cannot be continuously oscillated, the same treatment as in the large-size ophthalmologic photocoagulator of water cooling type can be conducted.

In such an ophthalmologic photocoagulator, for example, a He—Ne laser is used as the sighting laser oscillator and an argon laser or a dye laser is used as the treatment laser oscillator. In addition, there have been known an ophthalmologic photocoagulator in which the wavelength of observation laser beam for observing the eye to be examined is different from the wavelength of the sighting laser beam, and an ophthalmologic photocoagulator in which the wavelength of the observation laser beam is equal to or different from the wavelength of the treatment laser beam. Note that, in such ophthalmologic photocoagulators, a dichroic mirror is used as a combining means for combining the optical path of the treatment laser beam with the optical path of the sighting laser beam (see, for example, JP 07-163613 A (paragraphs [0019], [0025], and [0026] and FIG. 1)).

However, the following problems are generated in the conventional ophthalmologic photocoagulators. That is, when the eye fundus having a color similar to the red sighting laser beam is spotted with the red sighting laser beam, the visibility thereof is bad. Therefore, it is difficult to conduct sighting on the diseased part with high precision. In addition, when the dichroic mirror is used as the combining means for combining the optical path of the treatment laser beam with the optical path of the sighting laser beam, a loss in the amount of any one of the laser beams that is transmitted through the combining means has to become large (about 7%).

Also, from a view point that the dichroic mirror has a characteristic in which a loss in the amount of light in the case of light reflection is smaller than that in the case of light transmission, it is necessary for the ophthalmologic photocoagulator disclosed in JP 07-163613 A to ensure efficiency to reduce the loss in the amount of light by using as the treatment laser beam for which a high output is required as the laser beam to be reflected. This becomes one of factors limiting the degree of freedom in design of an apparatus.

SUMMARY OF THE INVENTION

The present invention has been made in view of the above-mentioned problems. Therefore, an object of the present invention is to provide an ophthalmologic photocoagulator in which visibility in a spot image of sighting laser beam which is formed onto the eye fundus of an eye to be examined is improved and a loss in the amount of laser beam traveling through a combining means, in particular, laser beam that is transmitted can be reduced to increase the degree of freedom in design of an apparatus.

In order to solve the above-mentioned problems according to a first aspect of the present invention, there is provided an ophthalmologic photocoagulator including:

a treatment laser oscillator for oscillating a treatment laser beam for conducting treatment on a diseased part of an eye to be examined by photocoagulation;

a sighting laser oscillator for oscillating a sighting laser beam for conducting sighting on the diseased part of the eye to be examined which is to be irradiated with the treatment laser beam; wherein the photocoagulator comprises further a combining means for combining an optical path of the treatment laser beam with an optical path of the sighting laser beam by polarization coupling and the treatment laser oscillator and the sighting oscillator oscillate laser beam having similar colors each other.

Further, according to a second aspect of the present invention, the ophthalmologic photocoagulator is characterized by further including a light receiving means for receiving a part of the treatment laser beam to monitor whether or not the treatment laser oscillator oscillates at a predetermined output.

Further, according to a third aspect of the present invention, an opthalmologic photocoagulation method in which a treatment laser beam is irradiated from a treatment laser beam oscillator and a sighting laser beam is irradiated from a sighting laser beam oscillator, comprising the steps of:

oscillating the treatment laser from the treatment laser beam oscillator, simultaneously the sighting laser beam from the sighting laser beam oscillator which have similar colors each other, and combining an optical path of the treatment laser beam and an optical path of the sighting laser beam by polarization coupling.

Further, according to a fourth aspect of the present invention, the ophthalmologic photocoagulation method is characterized in that a difference between a wavelength of the treatment laser beam oscillated from the treatment laser oscillator and a wavelength of the sighting laser beam oscillating from the sighting laser oscillator is equal to or smaller than 30 nm.

DETAILED DESCRIPTION OF THE PREFERRED EMBODIMENTS

Hereinafter, preferred embodiments of the present invention will be specifically described with reference to the drawings.

First Embodiment

Structure of Ophthalmologic Photocoagulator

Figure 1:
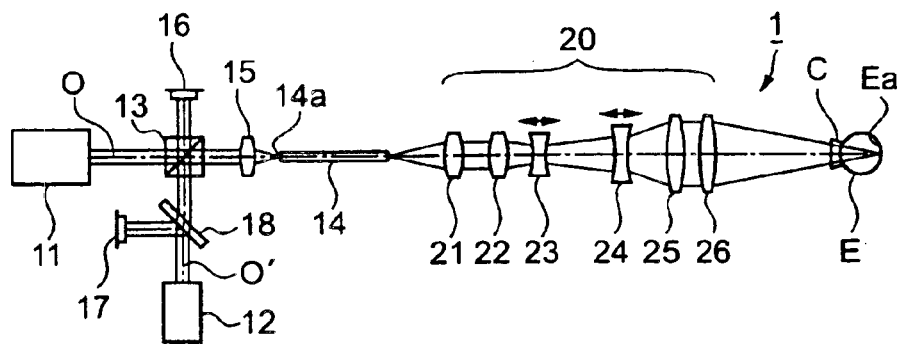
FIG. 1 is a schematic view showing an optical structure of an ophthalmologic photocoagulator according to a first embodiment of the present invention.

FIG. 1 is a schematic view showing an optical structure of an ophthalmologic photocoagulator 1 according a first embodiment of the present invention. The ophthalmologic photocoagulator 1 includes a treatment laser oscillator 11, a sighting laser oscillator 12, a polarization beam splitter 13, an optical fiber 14, a condenser lens 15, photo diodes 16 and 17, a glass plate 18, and a laser irradiation optical system 20.

The ophthalmologic photocoagulator 1 is provided with the two laser oscillators. The treatment laser oscillator 11 is a treatment laser oscillating means that oscillates treatment laser beam for conducting treatment to a diseased part on an eye fundus Ea of an eye to be examined E by photocoagulation. Further, the sighting laser oscillator 12 composes a sighting laser oscillating means that oscillates sighting laser beam for conducting sighting on the diseased part to be irradiated with the treatment laser beam.

The treatment laser oscillator 11 oscillates, as the treatment laser beam, green laser beam (green laser beam having, for example, 532 nm) in an optical axis O direction. On the other hand, the sighting laser oscillator 12 oscillates, as the sighting laser beam, green laser beam having the same wavelength as the treatment laser beam, that is, the same color as the treatment laser beam in an optical axis O' direction. The two laser oscillators 11 and 12 are connected with switches which are not shown, respectively. Therefore, the laser oscillators can be separately switched on/off by operating the switches. Each of the laser oscillators used here can be selected as appropriate from all kinds of lasers such as a gas laser, a solid-state laser, and a semiconductor laser, according to necessity. In addition, both the laser oscillators are not necessarily of the same kind and it is sufficient that the laser oscillators can oscillate the green laser beams having the same wavelength. Note that the term "same wavelength" indicates that the wavelength of the sighting laser beam is determined according to the wavelength of the treatment laser beam which is regarded as dominant and does not indicate that the wavelength of the treatment laser beam is determined according to the wavelength of the sighting laser beam.

The polarization beam splitter 13 is an optical element using doubly refracting crystal and has a function for separating an incident light flux into two directional light fluxes having oscillating directions orthogonal to each other. The polarization beam splitter 13 is used as a combining means for combining an optical path of the treatment laser beam with an optical path of the sighting laser beam by polarization coupling. When the polarization beam splitter 13 is used, a loss in the amount of laser beam, which is caused when passing through the combining means can be reduced. In particular, it is possible to efficiently reduce not only a loss in the amount of laser beam reflected by the polarization beam splitter 13 but also a loss in the amount of laser beam transmitting through the polarization beam splitter 13.

It is conceivable that a half mirror for light splitting is used as the combining means for combining two laser beams having the same wavelength. However, in such a half mirror, a loss in the amount of treatment laser beam is increased. Therefore, the half mirror is not a preferable alternative means for the ophthalmologic photocoagulator 1 of this embodiment.

The optical fiber 14 guides to the laser irradiation optical system the treatment laser beam and/or the sighting laser beam which is condensed to an incident end 14a of the optical fiber 14 by the condenser lens 15.

The photo diode 16 is a light receiving means that receives reflection light of the treatment laser beam which is produced by the polarization beam splitter 13. A part of the treatment laser beam received by the photo diode 16 is fed back as output monitoring data for determining whether or not the treatment laser oscillator 11 holds a normal output. Similarly, the photo diode 17 is used for feedback processing for monitoring the output of the sighting laser oscillator 12. In addition, the glass plate 18 is disposed such that a part of the sighting laser beam oscillated from the sighting laser oscillator 12 is made incident into the photo diode 17.

The laser irradiation optical system 20 is composed of a lens group (various lenses 21 to 26) incorporated in a slit lamp (not shown) that conducts observation, photographing, and the like on the eye to be examined E. The laser irradiation optical system 20 is an optical system which is used for leading to the eye to be examined E the treatment laser beam and/or the sighting laser beam which is guided through the optical fiber 14 and for irradiating the eye fundus Ea with the lead laser beam to form spot images. The lenses 23 and 24 are constructed to be movable in directions indicated by arrows in FIG. 1, respectively so that the sizes of spot images formed by irradiating the treatment laser beam and/or the sighting laser beam on the eye fundus Ea can be changed. Further, the lens 26 is an objective lens disposed opposite to the eye to be examined E and images the treatment laser beam and/or the sighting laser beam onto the eye fundus Ea to form spot images. In addition, a control lever for conducting precise sighting through the slit lamp and operation of shifting an observation region of the eye to be examined E is provided in the slit lamp as in a general case.

A contact lens C is used to observe the eye fundus Ea. The treatment laser beam and/or the sighting laser beam are applied to the eye fundus Ea through the contact lens C.

The treatment laser oscillator 11 and the sighting laser oscillator 12 are disposed such that the treatment laser beam and the sighting laser beam are made incident into the polarization beam splitter 13 from directions orthogonal to each other. In FIG. 1, assuming that the polarization beam splitter 13 is positioned at the center of a clock plate, the treatment laser oscillator 11 is disposed in the direction of 9 o'clock and the sighting laser oscillator 12 is disposed in the direction of 6 o'clock. In addition, the reflection direction of the treatment laser beam surface-reflected on the polarization beam splitter 13 is different from the incident direction of the treatment laser beam made incident into the polarization beam splitter 13 by 90 degrees in a clockwise direction (in the example using the clock dial, the reflection direction of the treatment laser beam is the direction of 12 o'clock).

Also, the traveling direction of the sighting laser beam which is oscillated from the sighting laser oscillator 12 in the optical axis O' direction is changed by 90 degrees in a counterclockwise direction by the polarization beam splitter 13. Accordingly, the sighting laser beam travels along the optical axis O, similar to the transmission light of the treatment laser beam. That is, polarization coupling is made between the treatment laser beam and the sighting laser beam by the polarization beam splitter 13. Therefore, the spot image of the treatment laser beam and the spot image of the sighting laser beam are aligned such that imaging positions of the spot images on the eye fundus Ea coincide with each other.

Operation of Ophthalmologic Photocoagulator

Hereinafter, the operation of the ophthalmologic photocoagulator 1 having the above-mentioned structure according to the first embodiment of the present invention will be described.

When treatment is to be conducted using the ophthalmologic photocoagulator 1, first, the eye to be examined E is opposed to the objective lens 26 of the above-mentioned slit lamp. An operator identifies a diseased part while observing a state of the eye fundus Ea of the eye to be examined E by the slit lamp.

Next, in order to conduct photocoagulation on the identified diseased part using the treatment laser beam, sighting is conducted on the diseased part. The operator turns on a switch which is not shown, to oscillate the sighting laser beam from the sighting laser oscillator 12. The oscillated sighting laser beam transmits through the glass plate 18 along the optical axis O' and is reflected by the polarization beam splitter 13, so that the traveling direction thereof is changed to the optical axis O direction. The reflected sighting laser beam is condensed by the condenser lens 15 and made incident into the incident end 14a of the optical fiber 14. The sighting laser beam thus guided to the slit lamp through the optical fiber 14 forms a spot image on the eye fundus Ea of the eye to be examined E by the laser irradiation optical system 20.

The operator operates the control lever of the slit lamp to align the spot image of the sighting laser beam with the identified diseased part, so that the sighting for irradiation of the treatment laser beam is conducted.

At this time, because the sighting laser beam is green laser beam, visibility of the spot image on a background, that is, on the eye fundus Ea having a red color is preferable, with the result that the operator can easily conduct the sighting on the diseased part. Accordingly, because rapid and precise sighting is possible, it is expected that a treatment time is shortened and mistreatment is reduced. In addition, a physical burden placed on a person to be treated and a mental burden placed on the operator are reduced.

After the sighting on the diseased part is completed, the treatment laser oscillator 11 is turned on to oscillate the treatment laser beam. The oscillated treatment laser beam is made incident into the polarization beam splitter 13 along the optical axis O, transmits therethrough, and then is condensed to the incident end 14a of the optical fiber 14 by the condenser lens 15. The treatment laser beam that transmits through the optical fiber 14 and reaches the laser irradiation optical system 20 is imaged onto the eye fundus Ea of the eye to be examined E to form a spot image, likewise the sighting laser beam. Thus, the treatment by photocoagulation is conducted.

As described above, both the treatment laser beam and the sighting laser beam travel on the same optical path along the optical axis O due to the polarization beam splitter 13. Accordingly, the photocoagulation can be precisely conducted on the diseased part on which the sighting is completed.

Now, in view of the singularity of polarization axes of the laser beams, when the polarization beam splitter 13 is disposed such that the polarization axis of the treatment laser beam and the transmission axis of the polarization beam splitter 13 become parallel to each other, most of the treatment laser beam transmit through the polarization beam splitter 13 and travel along the optical axis O. In addition, even when the polarization axis of the treatment laser beam and the transmission axis of the polarization beam splitter 13 cannot be made parallel to each other due to the limitation of arrangement, the polarization axis can be rotated by a ½ wavelength plate. At this time, a part of the treatment laser beam (1% to 2% of the entire amount of light) is reflected by the polarization beam splitter 13 to be made incident into the photo diode 16. The amount of light corresponding to 1% to 2% of the oscillated treatment laser beam is sufficient enough to be detected by the photo diode 16. In addition, in view of a loss in the amount of treatment laser beam, the amount corresponding to 1% to 2% of the whole treatment light is of a greatly reduced amount as compared with the amount corresponding to about 7% of the same in the case where a conventional dichroic mirror is used, so that light use efficiency in the apparatus is improved.

When the output of the treatment laser beam is desired to be further increased because of requirement in the treatment, the following method can be also used. As described above, the sighting laser beam has the same wavelength as the treatment laser beam and travels along the common optical axis O. Accordingly, when the sighting laser beam is used as auxiliary light for the treatment laser beam, an insufficient output of the treatment laser beam can be compensated. This can be applied to, for example, the case where a spot image of the treatment laser beam on the eye fundus Ea is set to a large size and photocoagulation is conducted at a time on a diseased part located across a wide range.

In this embodiment, the combining means composed of the polarization beam splitter 13 is constructed such that the traveling direction of the sighting laser beam is changed to coincide with the traveling direction of the treatment laser beam. However, the combining means may be constructed such that the treatment laser oscillator 11 and the sighting laser oscillator 12 are interchanged and the traveling direction of the treatment laser beam is changed to coincide with the traveling direction of the sighting laser beam. Further, because a loss in the amount of laser beam, resulting from the transmission and reflection of the laser beam becomes very small by using the polarization beam splitter 13, combining means is constructed such that polarization coupling is made between the treatment laser beam and the sighting laser beam by the polarization beam splitter 13. Accordingly, because the limitation on the arrangement of the treatment laser oscillator 11 and the sighting laser oscillator 12 is resolved, the degree of freedom in design of an apparatus is increased, so that a size of the apparatus can be further reduced.

Second Embodiment

Figure 2:
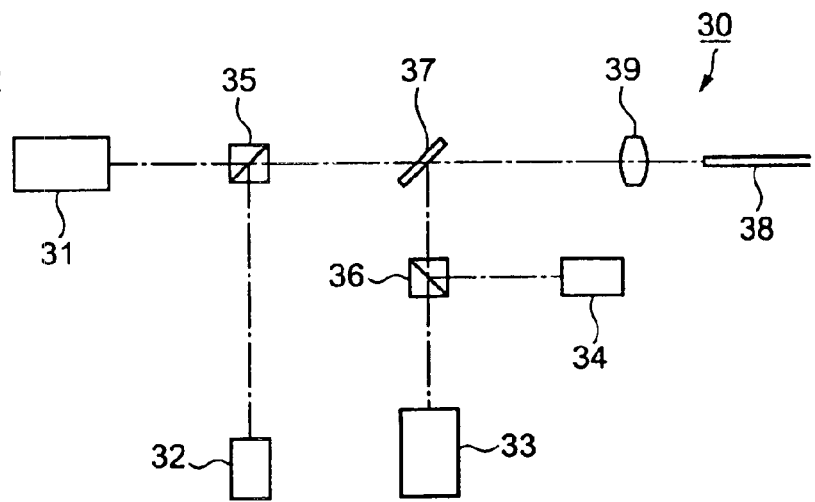
FIG. 2 is a schematic view showing an optical structure of an ophthalmologic photocoagulator according a second embodiment of the present invention.
Figure 3:
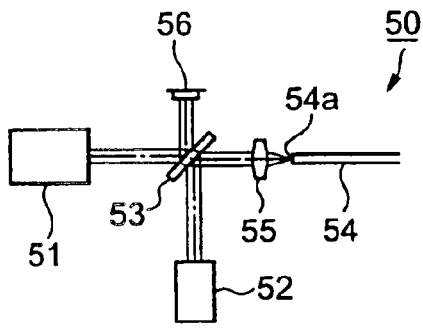
FIG. 3 is a schematic view showing an optical structure of a conventional ophthalmologic photocoagulator.

FIG. 2 is a schematic view showing an optical structure of an ophthalmologic photocoagulator 30 according to a second embodiment of the present invention. The ophthalmologic photocoagulator 30 is an apparatus for conducting treatment by photocoagulation using laser beams of plural colors and includes treatment laser oscillators 31 and 33, sighting laser oscillators 32 and 34, polarization beam splitters 35 and 36, a dichroic mirror 37, an optical fiber 38, and a condenser lens 39. It is possible that photo diodes are provided as in the ophthalmologic photocoagulator 1 of the first embodiment and feedback for output control is conducted. Note that laser beam incident into the optical fiber 38 is guided to a slit lamp to irradiate an eye to be examined. Because such operation is similar to that in the case of the ophthalmologic photocoagulator 1, the detailed description thereof is referred to the same case.

The treatment laser oscillators 31 and 33 oscillate treatment laser beams having different colors. The treatment laser oscillator 31 oscillates first treatment laser beam having a green color. The treatment laser oscillator 33 oscillates second treatment laser beam having a yellow color. An operator selects any one of the laser beams having colors based on a state of a diseased part on the eye fundus of the eye to be examined which is not shown.

The sighting laser oscillator 32 oscillates first sighting laser beam of a green color having the same wavelength as the first treatment laser beam. The sighting laser oscillator 34 oscillates second sighting laser beam of a yellow color having the same wavelength as the second treatment laser beam. In other words, the sighting for each treatment laser beam is conducted by using the sighting laser beam having the same color as the corresponding treatment laser beam.

According to such a structure, the operator can clearly recognize at a sighting stage which one of the treatment laser beams having the colors described above is to be used for photocoagulation. Therefore, a selection miss at the time of switching to the treatment laser beam and irradiation thereof can be effectively eliminated.

Also, it may be constructed such that only treatment laser beam having a color corresponding to sighting laser beam used for sighting can be oscillated following the oscillation of the sighting laser beam by on/off control of each of the laser oscillators.

Note that colors of laser beams to be used are not limited to the green color and the yellow color and therefore laser beams of various colors which are required for treatment can be selected as appropriate. In addition, colors of laser beams to be used are not limited to two kinds and therefore may be three or more kinds. Further, even when a treatment laser oscillator capable of oscillating plural kinds of laser beams is provided, a sighting laser oscillator capable of applying sighting laser beam having the same color as treatment laser beam may be provided.

According to the ophthalmologic photocoagulator 1 of the first embodiment and the ophthalmologic photocoagulator 30 of the second embodiment, as described above, it is assumed that the treatment laser beam and the sighting laser beam have the same wavelength. However, there may be a difference between wavelengths in which an operator recognizes that the color of the treatment laser beam is similar to the color of the sighting laser beam when projected onto the eye fundus. For example, in view of a hue recognizing ability of a human eye, although there are differences between individuals, if there is a difference of about 30 nm or less between the laser beams, the colors thereof are recognized as similar colors.

Note that, when employing the structure capable of applying plural kinds of treatment laser beams as in the second embodiment, it is preferable that the wavelength of the treatment laser beam and the wavelength of the sighting laser beam corresponding thereto are approximated to each other. More specifically, when the color of the treatment laser beam and the color of the sighting laser beam are further approximated to each other, a risk of misidentification with laser beam having another color is reduced. In particular, when laser beams to be used have many kinds of colors, the above-mentioned color approximation is preferable. Even in the case of the ophthalmologic photocoagulator 30, for example, if the first sighting laser beam has a green color close to a yellow color and the second sighting laser beam has a yellow color close to a green color, misidentification is liable caused. However, if each sighting laser beam has the same wavelength as the treatment laser beam or an approximate wavelength in which the color of the sighting laser beam is recognized as a color similar to the treatment laser beam, such misidentification is hardly caused.

Finally, the ophthalmologic photocoagulator as described in the second embodiment as an example includes one or plural treatment laser oscillators that oscillate plural colors of treatment laser beams and one or plural sighting laser oscillators that oscillate sighting laser beams for conducting sighting for the treatment laser beams. The ophthalmologic photocoagulator is characterized in that the sighting laser oscillators can oscillate sighting laser beams having colors similar to the plural colors of the treatment laser beams oscillated from the treatment laser oscillators.

The ophthalmologic photocoagulator having any structure described above in detail is just an example as the embodiment of the present invention. Therefore, the spirit of the present invention should be kept based on the above-mentioned embodiments. Thus, the spirit of the present invention should be determined according to claims.

As described above, according to the present invention, the color of the sighting laser beam and the color of the treatment laser beam are set to have similar colors. Therefore, it is possible that visibility of the spot image produced by the sighting laser beam on the eye fundus of the eye to be examined is improved, thereby easily conducting sighting on a diseased part. Thus, an ophthalmologic photocoagulator suitable for an operator that conducts treatment can be provided.

In addition, it is possible to shorten a time for the sighting, and accordingly shorten a treatment time. Thus, a burden placed on a person to be treated can be reduced.

Also, according to the present invention, a loss in the amount of light when the laser beam travels in (in particular, transmits through) the combining means is reduced. Thus, the degree of freedom in designing an ophthalmologic photocoagulator can be improved.

What is claimed is:

1. An ophthalmologic photocoagulator comprising:

a treatment laser oscillator for oscillating a treatment laser beam for conducting treatment by photocoagulation on a diseased part of an eye to be examined;

a sighting laser oscillator for oscillating a sighting laser beam for conducting sighting on the diseased part of the eye to be examined which is to be irradiated with the treatment laser beam;

a combining means for combining an optical path of the treatment laser beam with an optical path of the sighting laser beam by polarization coupling and the treatment laser oscillator and the sighting laser oscillator oscillate laser beams having similar colors to each other;

a first light receiving means for receiving a part of the treatment laser beam to monitor whether or not the treatment laser oscillator oscillates at a first predetermined output; and a second light receiving means for receiving a part of the sighting laser beam to monitor whether or not the sighting laser oscillator oscillates at a second predetermined output.

2. An ophthalmologic photocoagulation method, wherein a treatment laser beam is irradiated from a treatment laser beam oscillator and a sighting laser beam is irradiated from a sighting laser beam oscillator, comprising the steps of:

oscillating a treatment laser beam from the treatment laser beam oscillator;

simultaneously oscillating a sighting laser beam from the sighting laser beam oscillator, having a color similar to that of the treatment laser beam;

combining an optical path of the treatment laser beam and an optical path of the sighting laser beam by polarization coupling;

detecting a part of the treatment laser beam to monitor whether or not the treatment laser beam oscillator oscillates at a first predetermined output; and detecting a part of the sighting laser beam to monitor whether or not the sighting laser beam oscillator oscillates at a second predetermined output.

3. An ophthalmologic photocoagulation method according to claim 2, wherein a difference between a wavelength of the treatment laser beam oscillating from the treatment laser oscillator and a wavelength of the sighting laser beam oscillating from the sighting laser oscillator is equal to or less than 30 nm.

* * * * *